United States Patent
O'Leary et al.

(10) Patent No.: US 7,132,461 B2
(45) Date of Patent: Nov. 7, 2006

(54) PROCESS FOR PREPARING A GEL ELEMENT

(75) Inventors: Nicholas O'Leary, Southall (GB); Geraldine Lang, Slough (GB)

(73) Assignee: Reckitt Benckiser (UK) Limited, Slough (GB)

(*) Notice: Subject to any disclaimer, the term of this patent is extended or adjusted under 35 U.S.C. 154(b) by 21 days.

(21) Appl. No.: 10/492,807

(22) PCT Filed: Oct. 9, 2002

(86) PCT No.: PCT/GB02/04583

§ 371 (c)(1), (2), (4) Date: Sep. 28, 2004

(87) PCT Pub. No.: WO03/033038

PCT Pub. Date: Apr. 24, 2003

(65) Prior Publication Data

US 2005/0043432 A1 Feb. 24, 2005

(30) Foreign Application Priority Data

Oct. 16, 2001 (GB) .................................. 0124728.7

(51) Int. Cl.
*A61L 9/04* (2006.01)
(52) U.S. Cl. ...................................................... 523/102
(58) Field of Classification Search ................. 523/102
See application file for complete search history.

(56) References Cited

U.S. PATENT DOCUMENTS

| 5,780,527 A | 7/1998 | O'Leary et al. ............. 523/102 |
| 6,631,852 B1 | 10/2003 | O'Leary ...................... 239/60 |

FOREIGN PATENT DOCUMENTS

| WO | WO 96/05870 | 2/1996 |
| WO | WO 00/24434 | 5/2000 |

*Primary Examiner*—Edward J. Cain
(74) *Attorney, Agent, or Firm*—Norris McLaughlin & Marcus, P.A.

(57) ABSTRACT

The present invention relates to a process for preparing a gel element comprising a perfume and to a process for preparing an air freshening device comprising such a gel element.

11 Claims, No Drawings

PROCESS FOR PREPARING A GEL ELEMENT

The present invention relates to a process for preparing a gel element comprising a perfume and to a process for preparing an air freshening device comprising such a gel element.

Various devices for perfuming an atmosphere are known. Such devices may simply fragrance the air, or may be used to mask bad odours.

Many different types of air freshener devices have been proposed. One particular type is described in WO 96/05870 and WO 00/24434. This device comprises a gelled element resulting from the cross-linking between a functionalised liquid polymer and a cross-linking agent in the presence of a perfume base. In order to prepare such an element a liquid functionalised polymer is mixed with a cross-linking agent in the presence of a perfume. The polymer crosslinks in the presence of the perfume to form a gel which encloses the perfume, preferably in a three-dimensional network. Such a gel can be formed in a recess in a substrate to form an air freshener device, or can simply be used as a block. This gel has an attractive appearance. A large proportion of perfume base, for example up to 90 wt %, especially 60 to 90 wt %, may be used which provides a gel element of a small size.

In practice, the volume of crosslinking agent is small compared with the volume of perfume and polymer. For example, the crosslinking agent may be used in an amount of up to 2 vol % with respect to the total volume of components which are mixed together before gelling. While it is practicable to mix the perfume and polymer together to form a homogeneous mixture and then mix in the crosslinking agent, we have found that such an arrangement is not completely satisfactory because it is difficult to control the flow of the crosslinking agent in view of its relatively small volume.

We have therefore found that it is appropriate to equalise to a certain extent the flow rates of the different premixes into the final mixing step. Accordingly it is possible to form the perfume by conventional methods and then mix some of the perfume with the polymer and the remainder of the perfume with the crosslinking agent. The two mixtures can then be mixed together to form a mixture which is able to gel. Since the perfume is split between the two mixtures, the mixture containing the crosslinking agent has a greater volume than the volume of the crosslinking agent by itself, and therefore a greater flow rate which can easily be controlled.

We have now found that while this arrangement is satisfactory when the production line starts, it is not entirely satisfactory after the production line has been running for some time. It has been found that the gelling time of the mixture, i.e. the time required for a gel which does not flow to be formed, tends to rise over time. This can cause significant problems as the manufacturing shift progresses, especially at the end of a shift when a machine is operating. For example, if the gelling time of the mixture increases such that it is longer than the time that the containers containing the perfume element are on the production line, the gel may not have solidified to an acceptable extent and may still at least partly be in liquid form when the containers are removed from the line. This liquid can spill out of the containers leading not only to wastage but also to other problems such as fouling of the production line and local environment.

The present invention seeks to overcome this problem by providing a process in which the setting time of the mixture is reasonably constant over the time that a production machine is likely to operate, for example an eight hour shift or the length of time that the mixtures are stored before they are used, which is typically about four hours.

The present invention provides a process for preparing a gel element comprising a perfume which comprises:

i. forming a premix A of a liquid functionalised polymer and perfume components A;

ii. forming a premix B of a crosslinking agent able to crosslink said liquid functionalised polymer and perfume components B; and iii. mixing premix A and premix B such that said liquid functionalised polymer is crosslinked by said crosslinking agent in the presence of a perfume; wherein perfume components A are different from perfume components B, perfume components A do not substantially react with said liquid functionalised polymer and perfume components B do not substantially react with said crosslinking agent.

Perfumes usually contain components which react with either or both of the liquid functionalised polymer and the crosslinking agent. Accordingly in the process of the present invention the liquid functionalised polymer and crosslinking agent are mixed with different parts of the perfume, namely perfume components A and perfume components B, before they are mixed together. Thus the liquid functionalised polymer and crosslinking agents are not simply mixed with the same perfume composition. Instead the final perfume composition for the gelled element is determined, and different components of the composition are mixed with the liquid functionalised polymer and with the crosslinking agent. It has surprisingly been discovered that by ensuring an appropriate separation of perfume components, the above problem can be solved to a practical extent or even completely avoided. It is, of course, possible for some individual components which do not substantially react with either the liquid functionalised polymer or the crosslinking agent to be present in both perfume components A and perfume components B.

The perfume used in the process of the present invention is typically an anhydrous perfume, for example comprising less than 1 wt % water, especially less than 0.5 wt % water, more especially less than 0.1 wt % water and preferably comprising no water, and comprises a mixture of different ingredients. The perfume may simply provide a fragrance or it may provide a deodorising effect. While the precise ingredients of any particular perfume are often the trade secret of a Fragrance Supplier, it is well known that perfume ingredients are typically volatile compounds such as esters, alcohols, aldehydes and ketones. We have found that functionalised polymers and crosslinking agents can react with certain perfume ingredients. The rate of reaction may be relatively slow, so while this may not be a problem at the start of the production run, after the perfume ingredients have been mixed with the functionalised polymer and/or crosslinking agent for some time, for example after a few hours, some reaction will have occurred with some of the perfume components. This may undesirably affect the perfume so its fragrance is not constant over the full production run. Furthermore it will use up some of the functionalised polymer and/or crosslinking agent, which results in a reduction in the concentration of reactive sites of the functionalised polymer and/or the crosslinking agent after the production run has proceeded for some time. We have found that this leads to the increased setting time.

Apart from the splitting of the perfume into perfume components A and perfume components B, the process of the present invention is essentially as described in WO 96/05870 and WO 00/24434, which are herein incorporated by reference.

The liquid functional polymer possesses one or more functional groups. The crosslinking agent possesses two or more complimentary functional groups. The mixtures of these two compounds gives, in the presence of a perfume base, a reaction product enclosing the perfume base which can then emanate to the atmosphere to provide an air freshening effect. To obtain a three-dimensional network it is, however, necessary for the liquid functional polymer to have at least two functional groups per molecule.

The liquid functionalised polymer is one which is liquid at room temperature (20° C.) and which generally has a viscosity of not more than 5,000 poise at 25° C., preferably from 250 to 1,000 poise. The liquid functionalised polymer should be soluble in the perfume base. One or more liquid functionalised polymers may be used.

Suitable functional groups are, for example, carboxylic acid, anhydride or acid chloride groups as well as amine and alcohol groups. The polymer can be produced by adding functional groups to any polymer which is capable of functionalisation, or the polymer can be one which inherently contains functional groups, either pendent on the main chain, optionally with intervening spacer groups, or in the main chain. Preferred polymers which can be functionalised are polyolefins, particularly those derived from mono—or di-olefins containing, prior to functionalisation, at least one and preferably more than one vinyl group.

According to a preferred embodiment of the invention, the polymer is a derivative of butadiene, isoprene or chloroprene. Preferably the polymer is maleinised polybutadiene which may, for example, have a molecular weight of from 5000 to 20,000, or maleinised polyisoprene which may, for example, have a molecular weight of from 200,000 to 500,000. Such polymers are commercially available materials. Examples are disclosed in EP-A-23,084. A preferred polymer is sold under the trademark Lithene by Synthomer. A particularly preferred Lithene polymer is Lithene N4-9000 10MA, which is a maleinised polybutadiene wherein the molecular weight of the polybutadiene before maleinisation is about 9000 and which contains 10 parts of maleic anhydride per 100 parts of polybutadiene. Lithene N4-B-10MA has also been found to be particularly suitable.

The crosslinking agent possesses two or more complementary functional groups to the functional groups on the liquid functionalised polymer. The complementary functional groups may be, for example, carboxylic acid, anhydride or acid chloride derived groups or amine or alcohol groups. For example, if a liquid polymer possesses carboxylic acid, anhydride or acid chloride functionality, the crosslinking agents may have amine or alcohol functions, and vice versa. The crosslinking agent contains two, three or more functional groups. Preferably, however, it contains only two functional groups.

The crosslinking agent should be soluble in the perfume base. One or more crosslinking agents may be used. Examples of suitable crosslinking agents are dihydroxy polybutadiene, alkoxylated primary amines, alkylpropyldiamines having an ethoxylated or propoxylated fatty aliphatic chain, diethanolamine, diethylenetriamine, polyoxyalkylenediamines and alkoxylated primary fatty amines. For example the crosslinking agent may comprise one or more diamines and/or triamines, in particular one or more polyoxyalkylene amines, in particular diamines and triamines, such as polyethoxy diamines and triamines and/or polypropoxy diamines and triamines. Suitable ethoxylated primary amines are oleyl amines possessing two moieties of ethylene oxide per molecule.

Examples of alkylpropyldiamines having an ethoxylated or propoxylated higher aliphatic chain are those sold under the trademark Dicrodamet by Croda Chemicals Limited.

Examples of polyoxyalkylene diamines and/or triamines are polypropoxy diamines, polypropoxy triamines and polyethoxydiamines, particularly those sold under the trademark Jeffamine by Huntsman Corporation, for example Jeffamine D-400, Jeffamine D-2000, Jeffamine T-403 and Jeffamine EDR-148.

Further useful crosslinking agents are oleylamines or cocoamines having 2 to 5 ethylene oxide units per molecule, such as those sold under the trademark Crodamet by Croda Chemicals Limited, for example Crodamet 02 and Crodamet C5.

Additional useful crosslinking agent is polybutadiene having a hydroxylic function known as HFPB, obtainable from Revertex ltd. This crosslinking agent is especially suitable for use with maleinised polybutadiene.

Another suitable crosslinking agent is an amine terminated liquid butadiene/acrylonitrile copolymer, such as Hycar CTBN 1300×21, obtainable from B.F. Goodrich.

It is possible to use a mixture of two or more crosslinking agents having different reaction times with the liquid functionalised polymer in order to control the setting time of the gelled element.

The functionalised liquid polymer and crosslinking agent can be used in any molar ratio. Desirably, however, the molar ratio is from 3:1 to 0.5:1, preferably from 1.5:1 to 1:1.5, more preferably about 1:1, based on the molar ratio of the functional groups which are present. In general it is preferred to minimise the amount of unreacted functionalised polymer and crosslinking agent in the gelled element.

Catalysts can be included in premix A, premix B or in a further premix to assist in the gel formation. Examples of catalysts are tertiary amines, for example DAMA 1010 obtainable from Albemarle SA, and Jeffcat TD 100 or Jeffcat DMP, obtainable from Huntsman Corporation In general the mixture which gels comprise up to 90 wt % perfume base, especially 60 to 90 wt %, more especially 75 to 85 wt %, based on the total weight of the mixture. It also desirably comprises 8 to 35 wt %, especially 12 to 25 wt %, more especially 15 to 20 wt %, functionalised liquid polymer, based on the total weight of the mixture, and desirably also comprises 0.5 to 20 wt %, especially 0.5 to 6 wt %, more especially 0.7 to 4 wt %, crosslinking agent, based on the total weight of the mixture.

Further components can also be included in premix A, premix B or in a further premix. Such components can include, for example, additional perfume components, solvents, bitrex and dyes.

The perfume is a mixture of volatile liquid ingredients of natural or synthetic origin. The nature of these ingredients can be found in specialised perfumery books, for example in S. Arctander, Perfume and Flavour Chemicals, Montclair, N.J., USA, 1969. In order to carry out the process of the present invention, it is usual to carry out an initial step of devising a perfume having the desired fragrance. This is a routine operation which can be carried out by a Fragrance House.

In general it is the crosslinking agent which is able to react with some of the perfume components, whereas the liquid functionalised polymer usually does not appreciably react during the timescale of a production shift. In this case, therefore, those components of the perfume which react or are considered likely to react with the crosslinking agent form the basis of premix A. The remaining components which do not react or are considered unlikely to react with the crosslinking agent may form premix B. However, it is perfectly possible, and indeed usual, for some of these components which do not react with the crosslinking agent to be added to premix A. This may be useful to control the relative volumes of the premixes.

If the liquid functionalised polymer, but not the crosslinking agent, is able to react with some of the perfume components, those components of the perfume which react or are considered likely to react with the liquid functionalised polymer form the basis of premix B. The remaining components which do not react or are considered unlikely to react with the liquid functionalised polymer may form premix A. Again, it is perfectly possible for some of these components which do not react with the liquid functionalised polymer to be added to premix B.

Another way of proceeding is to determine the ingredients of the perfume and simply to take those a few of the components which are known not to react with the crosslinking agent to form premix B or which are known not to react with the liquid functionalised polymer to form premix A. All of the other components are then used to form premix A or premix B respectively.

Individual perfume components which do not react with either the liquid functionalised polymer or the crosslinking agent may, of course, be included in either or both of premix A and premix B.

In general it has been found that the aldehydes are capable of reacting with either the liquid functionalised polymer or the crosslinking agent. It is usual, therefore, for substantially all of the aldehydes to be present in premix B or premix A respectively. Similarly it has been found that ketones often react with the liquid functionalised polymer or crosslinking agent, although their rate of reaction is less than that of the aldehydes and some ketones do not react for steric reasons. We have found, therefore, that it is desirable for the ketones also to be present in the premix A or premix B which contains the aldehyde components. We have also found that alcohols, in particular primary alcohols, often react with the liquid functionalised polmyer or crosslinking agent. It is desirable, therefore, that the alcohols, or at least the primary alcohols and optionally secondary alcohols and/or tertiary alcohols, are present in the premix A or premix B respectively. It is particularly desirable for the premix A or premix B not to contain aldehydes, and preferably also not to contain ketones, when the liquid functionalised polymer or crosslinking agent, respectively, contains amine groups.

In a preferred embodiment where the liquid functionalized polymer is a maleinised polybutadiene and the crosslinking agent is one or more polyoxyalkylene diamines, it has been found that aldehydes in particular can react with the crosslinking agent. It is usual, therefore, for substantially all of the aldehydes to be present in premix A. Similarly it has been found that ketones also react with the crosslinking agent, although their rate of reaction is less than that of the aldehydes. We have found therefore that it is also desirable for ketones to be present in premix A, which contains the aldehyde components. It has also been found that primary alcohols will react with the maleic anhydride moeities of the liquid functionalised polymer and it is usual therefore for substantially all primary alcohols to be present in premix B.

In the present invention it is necessary for the perfume components A and perfume components B not to substantially react with the liquid functionalised polymer and crosslinking agent respectively. By this we mean that the components within each premix do not appreciably react together before each batch is fully used. Clearly this will depend on a certain extent to the time taken for each batch of premix to be fully used and the gelling time allowed on the production line. In general, however, each premix is stable at room temperature (20° C.) for at least 2 hours, preferably at least 4 hours, more preferably at least 6 hours and most preferably at least 8 hours.

By stable we mean that substantially no reaction occurs between the perfume components and the remaining components of the premix during this period. It is, therefore, possible for premix A and/or premix B to contain some fragrance components which are capable of reacting slowly with the liquid functionalised polymer or crosslinking agent, respectively, but which do not appreciably react within the time that the premixes are stored before use. Alternatively it is, of course, possible for the premix A or premix B to contain small quantities of components which react with the liquid functionalised polymer or crosslinking agent, respectively, so long as these do not appreciably reduce the amount of liquid functionalised polymer or crosslinking agent which is available for reaction. If any reaction does occur, the reaction only occurs to an extent that the gelling time to achieve a solid, non-flowable gel increases only slightly, for example by up to 20%, preferably up to 10%, more preferably up to 5%. For example, if the initial gelling time at the beginning of a production run is 6 minutes, desirably the gelling time increases at most to 7 minutes 12 seconds, preferably at most to 6 minutes 32 seconds and more preferably at most to 6 minutes 18 seconds. These times are all significantly shorter than the increased gelling time of about 10 minutes which can be achieved if the perfume components are not split between the different premixes.

Desirably the premix A and/or premix B contain less than 1 wt %, preferably less than 0.5 wt % of components which react with the liquid functionalised polymer or crosslinking agent respectively. More desirably, the premix A and/or premix B contains no aldehydes and/or ketones and/or primary alcohols as appropriate.

We have also found that the process of the present invention can surprisingly reduce the formation of undesirable side products which can otherwise be formed during the process. For example, it was previously noticed that certain premixes could become cloudy, and even lack phase stability. We have now determined that this was due to certain perfume components, in particular aldehydes, reacting with groups on the liquid functionalised polymer or crosslinking agent, in particular amine groups, especially primary amine groups, to form a substituted imine and water. This water is not usually miscible with the anhydrous perfume base and hence the perfume base becomes cloudy. In extreme situations, the water can even form a second phase. In some cases certain components, such as the substituted imines, can precipitate from solution which can cause blockages in the production machinery. The process of the present invention surprisingly also overcomes this disadvantage since the in situ formation of water and other components such as imines is substantially avoided.

Desirably the mixture gels (i.e. forms a non-flowable solid) in step iii in less than 8 minutes during the entire production run, preferably from 4 to 8 minutes, more preferably from 6 to 7 minutes.

The weight ratio of premix A to premix B is desirably from 2:1 to 8:1, for example from 3:1 to 6:1, especially from 4:1 to 5:1. The weight ratio of perfume components A to perfume components B is desirably from 2:1 to 6:1, preferably from 3:1 to 5:1.

The gel element is desirably formed by adding the mixture of premix A and premix B to a mould, for example a recess in a substrate, and allowing the mixture to gel. Examples of suitable substrates and forms for the recess are given in WO 00/24434.

The present invention is further described in the following Examples.

EXAMPLES

Comparative Example 1

The following fragrance was prepared:

| Ingredient | % w/w |
| --- | --- |
| Isobornyl acetate | 25.00 |
| Dihydromyrcenol* | 25.00 |
| tertiary-4-Butylcyclohexyl acetate | 15.00 |
| Orange oil terpenes | 10.00 |
| Terpinyl acetate | 4.00 |
| Eucalyptus oil | 4.00 |
| Isopentyrate** | 3.00 |
| Juniperberry oil | 2.50 |
| Lavandin oil | 2.00 |
| Allyl Caproate | 2.00 |
| Dynascone** | 1.00 |
| alpha-iso-Methyl ionone | 1.00 |
| Geranium oil | 1.00 |
| Applinate** | 1.00 |
| Verdox* | 1.00 |
| n-Dodecanal | 0.50 |
| 2-methyl undecanal | 0.50 |
| Coriander oil | 0.50 |
| Rosemary oil | 0.50 |
| Galbanum oil | 0.25 |
| 2,4-Dimethylformyl-3-cyclohexene | 0.20 |
| Oxane** (50% in triethylcitrate) | 0.05 |
| | 100.00 |

*Origin: International Flavors & Fragrances Inc.
**Origin: Firmenich S.A.

A cross-linking composition was prepared comprising 8.00 g Jeffamine D-400 and 4.40 g Jeffamine EDR-148.

Premix A was prepared by mixing 14.26 g of Lithene N4-B-10MA and 53.68 g of the entire fragrance in a closed 120 ml glass powder jar using a magnetic stirrer until the Lithene had completely dissolved. Premix B was prepared by mixing 1.02 g of the formerly prepared cross-linking composition and 14.92 g of the entire fragrance in a 20 ml glass vial. The time was then recorded (t=0).

After 10 minutes had elapsed 16.2 g of the Lithene/perfume mixture was transferred to a 50 ml glass beaker, and continually mixed with a magnetic stirrer. 3.8 g of the perfume/cross-linking composition was then added under constant stirring. The setting time of the gel thus produced was then measured.

This process was repeated when approximately 30 minutes, 4 hours and seven hours had elapsed. The gel setting times recorded are shown in Table 1.

TABLE 1

| Elapsed Time | Gel Setting Time |
| --- | --- |
| 10 minutes | 8 min 12 sec |
| 30 minutes | 9 min 40 sec |
| 4 hours | 11 min 5 sec |
| 7 hours | 13 min 5 sec |

Example 2

The same fragrance composition of Comparative Example 1 was prepared as two separate compositions, Perfume Components A and Perfume Components B, in which all of the aldehydes and ketones were in Perfume Components A.

Perfume Components A

| Ingredient | % w/w |
| --- | --- |
| Isobornyl acetate | 25.00 |
| Dihydromyrcenol* | 25.00 |
| Orange oil terpenes | 10.00 |
| Terpinyl acetate | 4.00 |
| Eucalyptus oil | 4.00 |
| Juniperberry oil | 2.50 |
| Lavandin oil | 2.00 |
| Dynascone** | 1.00 |
| alpha-iso-Methyl ionone | 1.00 |
| Geranium oil | 1.00 |
| n-Dodecanal | 0.50 |
| 2-methyl undecanal | 0.50 |
| Coriander oil | 0.50 |
| Rosemary oil | 0.50 |
| Galbanum oil | 0.25 |
| 2,4-Dimethylformyl-3-cyclohexene | 0.20 |
| Oxane** (50% in triethylcitrate) | 0.05 |
| | 78.00 |

*Origin: International Flavors & Fragrances Inc.
**Origin: Firmenich S.A.

Perfume Components B

| Ingredient | % w/w |
| --- | --- |
| Tertiary-4-Butylcyclohexyl acetate | 15.00 |
| Isopentyrate** | 3.00 |
| Allyl Caproate | 2.00 |
| Applinate** | 1.00 |
| Verdox* | 1.00 |
| | 22.00 |

*Origin: International Flavors & Fragrances Inc.
**Origin: Firmenich S.A.

Premix A was prepared by mixing 14.55 g of Lithene N4-B-10MA and 54.78 g of Perfume Component A in a closed 120 ml glass powder jar using a magnetic stirrer until the Lithene had completely dissolved. Premix B was prepared by mixing 1.04 g of the cross-linking composition (as in Comparative Example 1) and 15.22 g of Perfume Component B fragrance in a 20 ml glass vial. The time was then recorded (t=0).

After 10 minutes had elapsed 16.2 g of the Lithene/perfume mixture was transferred to a 50 ml glass beaker, and continually mixed with a magnetic stirrer. 3.8 g of the perfume/cross-linking composition was then added under constant stirring. The setting time of the gel thus produced was then measured.

This process was repeated when approximately 30 minutes, 4 hours and seven hours had elapsed. The gel setting times recorded are shown in Table 2.

TABLE 2

| Elapsed Time | Gel Setting Time |
| --- | --- |
| 10 minutes | 7 min 31 sec |
| 30 minutes | 7 min 17 sec |
| 4 hours | 7 min 40 sec |
| 7 hours | 8 min 30 sec |

The invention claimed is:

1. A process for preparing a gel element comprising a perfume which comprises the steps of:
   i. forming a premix A of a liquid functionalised polymer and perfume components A;
   ii. forming a premix B of a crosslinking agent able to crosslink said liquid functionalised polymer and perfume components B; and
   iii. mixing premix A and premix B such that said liquid functionalised polymer is crosslinked by said crosslinking agent in the presence of a perfume;

wherein perfume components A are different from perfume components B, perfume components A do not substantially react with said liquid functionalised polymer and perfume components B do not substantially react with said crosslinking agent.

2. A process according to claim 1 wherein the crosslinking agent comprises one or more diamines.

3. A process according to claim 2 wherein the crosslinking agent comprises one or more polyoxyalkylenediamines.

4. A process according to claim 1 wherein the liquid functionalised polymer comprises carboxylic, anhydride or acid chloride groups.

5. A process according to claim 1 wherein the liquid functionalised polymer is a maleinised polybutadiene and/or polyisoprene.

6. A process according to claim 1 wherein the weight ratio of premix A to premix B is from 2:1 to 8:1.

7. A process according to claim 1 wherein the weight ratio of perfume components A to perfume components B is from 2:1 to 6:1.

8. A process according to claim 1 wherein the mixture gels in step iii in less than 8 minutes during the entire production run.

9. A process according to claim 1 wherein premix A is stable at room temperature (20° C.) for at least 4 hours.

10. A process according to claim 1 wherein premix B is stable at room temperature (20° C.) for at least 4 hours.

11. A process according to claim 1 wherein the gel element is formed in a recess in a substrate to form an air freshening device.

* * * * *